United States Patent
Vaid et al.

(10) Patent No.: US 10,119,158 B2
(45) Date of Patent: Nov. 6, 2018

(54) PROCESS FOR THE PREPARATION OF FIDAXOMICIN

(71) Applicant: CONCORD BIOTECH LIMITED, Gujarat (IN)

(72) Inventors: Ankur Sudhir Vaid, Gujarat (IN); Mitesh Jagdishkumar Patel, Gujarat (IN); Dhimant Punjalal Mehta, Gujarat (IN); Anand Mahadev Dhiman, Gujarat (IN); Jayesh Chandubhai Patel, Gujarat (IN); Traunkant Parshuram Sharma, Gujarat (IN)

(73) Assignee: CONCORD BIOTECH LIMITED, Gujarat (IN)

( * ) Notice: Subject to any disclaimer, the term of this patent is extended or adjusted under 35 U.S.C. 154(b) by 0 days.

(21) Appl. No.: 14/785,696

(22) PCT Filed: Apr. 21, 2014

(86) PCT No.: PCT/IN2014/000251
§ 371 (c)(1),
(2) Date: Oct. 20, 2015

(87) PCT Pub. No.: WO2014/174528
PCT Pub. Date: Oct. 30, 2014

(65) Prior Publication Data
US 2016/0083764 A1 Mar. 24, 2016

(30) Foreign Application Priority Data

Apr. 23, 2013 (IN) .......................... 1498/MUM/2013

(51) Int. Cl.
*C12P 19/58* (2006.01)
*C07D 407/14* (2006.01)
*C12P 19/62* (2006.01)
*C07H 17/08* (2006.01)
*C12N 1/20* (2006.01)

(52) U.S. Cl.
CPC ............ *C12P 19/58* (2013.01); *C07D 407/14* (2013.01); *C07H 17/08* (2013.01); *C12N 1/20* (2013.01); *C12P 19/62* (2013.01)

(58) Field of Classification Search
CPC ........ C12P 19/58; C12P 19/62; C07D 407/14; C12N 1/20; C07H 17/08
See application file for complete search history.

(56) References Cited

U.S. PATENT DOCUMENTS 3,978,211 A * 8/1976 Coronelli .................. C12P 1/06
424/120
4,169,887 A * 10/1979 Celmer ...................... C12P 1/06
424/115
4,918,174 A * 4/1990 McAlpine .............. C07H 15/10
536/16.8

OTHER PUBLICATIONS

Erb et al. "From natural product to marketed drug: the tiacumicin odyssey". Nat Prod. Rep. 2013, 30, pp. 161-174 (published Oct. 30, 2012).*
Venugopal et al "Fidaxomicin: A Novel Macrocyclic Antibiotic Approved for Treatment of Clostridium difficile Infection". Clinical Infectious Diseases 2012; 54 (4): 568-74.*

* cited by examiner

*Primary Examiner* — Vera Afremova
(74) *Attorney, Agent, or Firm* — Blank Rome LLP

(57) ABSTRACT

The present invention provides an improved process for the preparation of fidaxomicin by culturing *Actinoplanes deccanensis* in the culture medium of the invention wherein the fidaxomicin is produced in a yield of greater than 500 mg/L broth. The present invention also provides a whole broth extraction process for the isolation of fidaxomicin from the fermentation broth. The present invention also provides fidaxomicin having purity of greater than 97% area by HPLC.

5 Claims, 3 Drawing Sheets

PROCESS FOR THE PREPARATION OF FIDAXOMICIN

FIELD OF THE INVENTION

The present invention provides an improved process for the preparation of fidaxomicin.

BACKGROUND OF THE INVENTION

J. Antibiotics 28, 247, 1975 describes the production of lipiarmycins from *Actinoplanes deccanensis* nov. sp. A/10655. Structural study of lipiarmycin A3, A4, B3 and B4 is described in *J. Antibiotics* 36, 1312, 1983 and *J. Antibiotics* 41, 308, 1988. Another article *J. Antibiotics* 39, 1407, 1986 describes strain *Micromonospora echinospora* subsp. *armeniaca* subsp. nov. KMR-593 to produce five antibiotics compounds named as clostomicin A, B1, B2, C and D. Another complex of six antibiotic compounds, named as tiacumicins (A-F), is produced from *Dactylosporangium aurantiacum* subspecies *hamdenensis* as described in *J. Antibiotics* 40, 567, 1987. Lipiarmycin A3, Clostomicin B1 and Tiacumicin B are the same compound, alternatively known as fidaxomicin, and have potent activity against *Clostridium difficile*.

U.S. Pat. No. 4,918,174 discloses six tiacumicin compounds (tiacumicin A-F) of the following chemical structure (I). Tiacumicin A-F has different substituent at R, $R_1$ and $R_2$ positions.

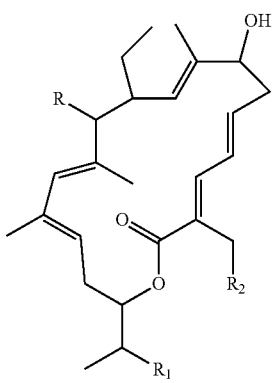

*Antimicrob. Agents Chemother.* 1991, 1108-1111 describes potent activity of tiacumicins, particularly tiacumicin B against *Clostridium difficile*.

U.S. Pat. No. 4,918,174 and *J. Antibiotics*, 1987, 575-588 describe production and isolation of tiacumicin B by aerobic fermentation of *Dactylosporangium aurantiacum* subspecies *hamdenensis*. Fermentation is carried out using glucose and soybean oil as a carbon source; and soybean flour, beef extract or peptone as a nitrogen source. Temperature is maintained in a range of 25 to 35° C. and pH is set in a range of 6 to 9. The filtered broth is extracted with ethyl acetate and is concentrated to give oily residue. The residue is purified by partitioning between solvents and chromatography. This process produces Tiacumicin B in maximum yield of 4.24 mg/L broth.

U.S. Pat. No. 7,507,564 provides an improved process for the preparation of fidaxomicin which gives better yield of fidaxomicin as compared to process disclosed in U.S. Pat. No. 4,918,174. The process of U.S. Pat. No. 7,507,564 gives more than 50 mg/L broth yield of fidaxomicin. According to U.S. Pat. No. 7,507,564, it is essential to use adsorbent resin in nutrient media during fermentation which leads to increased yield of fidaxomicin.

There is a need to develop a simpler process which provides increased yield of fidaxomicin.

US2010/0009925 describes stereomerically pure fidaxomicin, which contains >90% pure R isomer. However, it does not provide any method for its preparation, but referred to a process disclosed in U.S. Pat. No. 7,507,564. Fidaxomicin is chemically represented by structure of formula (II).

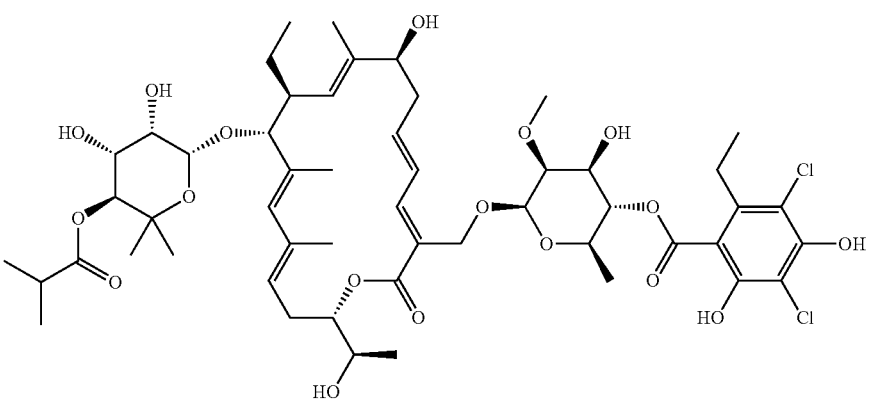

OBJECT OF THE INVENTION

An object of the present invention is to provide a culture medium for the production of fidaxomicin.

Another object of the present invention is to provide an improved process for the production of fidaxomicin comprising culturing fidaxomicin producing microorganism in the culture medium of the invention.

Another object of the present invention is to provide a process for the production of fidaxomicin in a yield of greater than 500 mg/L broth.

Yet another object of the present invention is to provide a process for the production of fidaxomicin in a yield of greater than 1000 mg/L broth.

Yet another object of the present invention is to provide a fermentation broth produced by culturing fidaxomicin producing microorganism wherein the broth provides fidaxomicin in a yield of greater than 500 mg/L broth.

Yet another object of the present invention is to provide a fermentation broth produced by culturing fidaxomicin producing microorganism wherein the broth provides fidaxomicin in a yield of greater than 1000 mg/L broth.

Further object of the present invention is to provide a process for a whole broth extraction of fidaxomicin.

Another object of the present invention is to provide fidaxomicin having purity of greater than 97% area by HPLC.

Yet another object of the present invention is to provide fidaxomicin having purity of greater than 98% area by HPLC.

Yet another object of the present invention is to provide fidaxomicin having purity of greater than 99% area by HPLC.

SUMMARY OF THE INVENTION

The present invention provides an improved process for preparation of fidaxomicin by culturing fidaxomicin producing microorganism, for example *Actinoplanes deccanensis* in a culture medium. The culture medium comprises of sorbitol as a carbon source and corn gluten as a nitrogen source. The fermentation broth, thus produced, provides fidaxomicin in a yield of greater than 500 mg/L broth. Fidaxomicin is isolated from the fermentation broth by whole broth extraction process. The crude fidaxomicin is purified by one or more methods selected from chromatography and/or crystallization. The process of the present invention provides fidaxomicin having purity of greater than 97% area by HPLC.

DETAILED DESCRIPTION OF THE INVENTION

Figure 1:
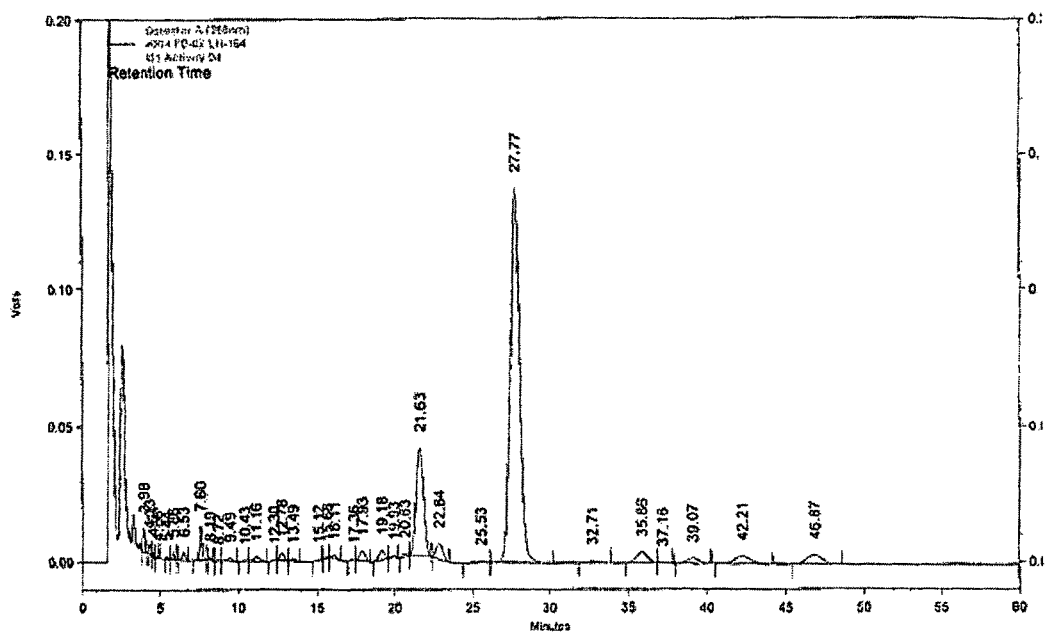
FIG. 1 refers to HPLC chromatogram showing yield of fidaxomicin obtained in Example 1.

The nature of the invention along with various components they are described in the following pages of the provisional specification.

The term "culture medium" refers to a liquid or gel media containing nutrients to support the growth of a microorganism. In general, a culture medium comprises one or more carbon source, one or more nitrogen source, inorganic salt(s) and optionally other growth ingredients.

The term "broth" refers to a fluid medium obtained due to fermentation. Broth comprises water, desired and/or undesired fermentation product(s), microorganism, unused nutrient and inorganic salts.

The term "fidaxomicin producing microorganism" refers to a microorganism capable of producing fidaxomicin, for example *Actinoplanes deccanensis* or a mutant strain thereof.

The term "fidaxomicin containing whole broth" refers to a whole broth produced by fermentation of the fidaxomicin producing microorganism.

The term "whole broth extraction" or "extracting a whole broth" refers to a process of extraction of a broth wherein the broth is not processed for filtration/isolation of any broth ingredient.

In a general process, fidaxomicin containing whole broth is extracted one or more time with a water immiscible organic solvent and product is isolated from the water immiscible organic solvent layers. The product obtained at this stage is termed as "crude fidaxomicin". The crude product is purified by chromatographic and/or crystallization techniques. The product obtained after purification is termed as "pure fidaxomicin". Pure fidaxomicin is characterized by a purity of at least greater than 97% area by HPLC.

The term "yield" refers to an amount of fidaxomicin in mg per liter of broth. The yield is calculated by HPLC method.

The terms "lipiarmycin A3", "clostomicin B1", "tiacumicin B" and "fidaxomicin" relates to the same compound of structural formula II.

Culture Medium

U.S. Pat. No. 7,507,564 describes a culture medium comprising fish powder, glucose, inorganic salts and adsorbent resin which provides crude fidaxomicin in a yield of greater than 50 mg/L broth. The said culture medium requires use of adsorbent resin.

The present invention provides an improved culture medium for the production of fidaxomicin. The culture medium of the invention is used for culturing fidaxomicin producing microorganism to produce fidaxomicin in a yield of greater than 500 mg/L broth. Although the culture medium of the invention does not require use of any adsorbent resin, it provides fidaxomicin in a yield which is greater than reported in prior art.

In one embodiment, the culture medium comprises sorbitol as a carbon source, corn gluten as a nitrogen source and one or more inorganic salt to support the microorganism growth.

Preferably sorbitol is present in the culture medium in an amount of about 0.1% to about 15% by weight. Most preferably sorbitol is present in an amount of about 1% to about 10% by weight.

Preferably corn gluten is present in the culture medium in an amount of about 0.1% to about 10% by weight. Most preferably corn gluten is present in an amount of about 0.5% to about 5% by weight.

The culture medium may also include additional one or more carbon and/or nitrogen source. Additional carbon sources added to the culture medium includes but are not limited to glucose, glycerol, cane sugar, soybean oil, starch and the like.

Additional nitrogen sources added to the culture medium includes but are not limited to peptone, beef extract, yeast extract, hot soybean powder, corn steep liquor, dry yeast cell powder, casein and the like.

Inorganic salts added to support the microorganism growth include but are not limited to $CaCO_3$, $MgSO_4.7H_2O$, $K_2HPO_4$, KCl and the like.

The culture medium may include other growth ingredients. Antifoam agent is optionally added to the culture medium to avoid the foaming problems.

Preferably, the culture medium comprises sorbitol, corn gluten, cane sugar, glycerol, soybean oil, hot soybean powder, dry yeast cell powder, $CaCO_3$, $MgSO_4.7H_2O$, KCl and $K_2HPO_4$. Most preferably, the culture medium comprises about 0.1% to about 15% wt of sorbitol, about 0.1% to about 10% wt of corn gluten, about 0.1% to about 15% wt of cane sugar, about 0.1% to about 5% wt of glycerol, about 0.1% to about 5% wt of soybean oil, about 0.1% to about 5% wt of hot soybean powder, about 0.1% to about 5% wt of dry yeast cell powder, about 0.05% to about 3% wt of $CaCO_3$, about 0.05% to about 2% wt of $MgSO_4.7H_2O$, about 0.05% to about 2% wt of KCl and about 0.01% to about 1% wt of $K_2HPO_4$.

Process for Producing Fidaxomicin

An embodiment of the invention provides an improved process for producing fidaxomicin which comprises culturing fidaxomicin producing microorganism in the culture medium of the invention. One example of the fidaxomicin producing microorganism is *Actinoplanes deccanensis* or a mutant strain thereof. Other microorganisms capable of producing fidaxomicin are also included within the scope of the invention, but *Actinoplanes deccanensis* is preferred. Preferably, culturing step is performed at a temperature from about 20° C. to 35° C. Most preferably, culturing step is performed at a temperature from about 25° C. to about 30° C. pH of the culturing step is maintained between about 5 to about 9. Preferably pH is maintained between about 6 to about 8. Culturing of a microorganism is continued for about 4 to about 12 days. Culturing of microorganism can be carried out in vessel ranging from a small fermentation flask to a large batch fermentation tank. In a general process, seed flask is inoculated with small amount of a microorganism. Vegetative growth produced, is then transferred to a fermentation tank and incubated to produce a whole broth containing fidaxomicin. The process of the invention provides fidaxomicin in a yield of greater than 500 mg/L broth, preferably greater than 1000 mg/L broth. Improved culture medium and process of the invention provides high yield of the fidaxomicin as compared to prior art processes.

In one embodiment, the present invention provides a process for a whole broth extraction of fidaxomicin which comprises
  a) extracting fidaxomicin containing whole broth with a water immiscible organic solvent wherein fidaxomicin is extracted into the water immiscible organic solvent from the fidaxomicin containing whole broth;
  b) separating the water immiscible organic solvent layer;
  c) isolating fidaxomicin from the water immiscible organic solvent layer.

Whole broth extraction does not require filtration or removal of mycelia mass from the broth and fidaxomicin is easily extracted into a water immiscible organic solvent from the whole broth. Preferably, the water immiscible organic solvent comprises an ester, an aromatic or aliphatic hydrocarbon or a $C_4$-$C_8$ alcohol. Most preferably, the water immiscible organic solvent is selected from ethyl acetate, isopropyl acetate, butyl acetate, toluene or isobutanol. Preferably, whole broth extraction is performed at a pH in a range of about 5 to about 9 and at a temperature in a range of about 20° C. to 35° C. Upon completion of extraction, the water immiscible organic solvent layer is separated and extraction process is repeated if required. For isolation of the product, the water immiscible organic solvent layers are combined and the solvent is evaporated to produce an oily residue. The oily residue is treated with an organic solvent to precipitate fidaxomicin which is filtered and dried to give crude fidaxomicin. The organic solvent is selected from alcohol, hydrocarbon and ether. Crude fidaxomicin is further purified by one or more methods selected from column chromatography, preparative HPLC and crystallization.

In one embodiment, the present invention provides a fermentation broth produced by culturing fidaxomicin producing microorganism wherein the broth provides crude fidaxomicin in a yield of greater than 500 mg/L broth, preferably greater than 1000 mg/L broth. The high yield of fidaxomicin as compared to prior art processes is obtained due to improved culture medium and production method of the invention.

In one embodiment the present invention provides a process for producing fidaxomicin which comprises
  a) culturing fidaxomicin producing microorganism in a culture medium wherein the culture medium comprises sorbitol, corn gluten and one or more inorganic salts to produce a whole broth containing fidaxomicin;
  b) extracting the whole broth with a water immiscible organic solvent;
  c) evaporating the water immiscible organic solvent to give residue;
  d) adding a second organic solvent to the residue to precipitate fidaxomicin;
  e) isolating crude fidaxomicin;
  f) purifying the crude fidaxomicin by chromatography and/or crystallization.

The production method of the invention advantageously produces fidaxomicin having high purity and reduced amount of related compounds. In one embodiment, the present invention provides fidaxomicin having purity of greater than 97% area by HPLC. In another embodiment, the present invention provides fidaxomicin having purity of greater than 98% area by HPLC. In another embodiment, the present invention provides fidaxomicin having purity of greater than 99% area by HPLC.

EXAMPLES

The following examples are presented to illustrate the invention and do not limit the scope of the invention. It should be understood that although specific embodiments are outlined in the examples, modifications can be made which are included within the scope of the invention.

Example-1

*Actinoplanes deccanensis* was maintained on medium M-1 PM-1 as defined in Table 1.

TABLE 1

| Culture storage medium Medium M-1 PM-1 | |
|---|---|
| Ingredient | (%) |
| yeast extract | 0.4 |
| malt extract | 1 |

TABLE 1-continued

| Culture storage medium Medium M-1 PM-1 | |
|---|---|
| Ingredient | (%) |
| glucose | 0.4 |
| agar | 2 |
| pH | 7.0 |

After sterilization conditions (40 min., 121° C., 1.05 kg/cm2) the seed flask (250 ml) containing medium M-1 NS2 (30 ml), as defined in Table 2, was inoculated with *Actinoplanes deccanensis* and incubated on rotary shaker (set at 220 rpm) at 28° C. for 24-28 hrs.

TABLE 2

| Seed medium for Shake flask Medium M-1 NS2 | |
|---|---|
| Ingredients | % |
| corn starch | 2 |
| glucose | 3 |
| yeast extract | 1 |
| beef extract | 0.5 |
| Soya peptone | 1 |
| $CaCO_3$ | 0.4 |
| $MgSO_4 \cdot 7H_2O$ | 0.2 |
| pH | 7.5 |

Five percent vegetative growth from the first passage seed flask was then transferred aseptically to a fermentation flask (250 ml) containing medium M-1 NP1 (30 ml) as defined in Table 3.

TABLE 3

| Culture medium Medium M-1 NP1 | |
|---|---|
| Ingredients | (%) |
| Cane sugar | 7 |
| sorbitol | 2 |
| glycerol | 2 |
| soybean oil | 0.5 |
| corn gluten | 1 |
| hot soybean powder | 1.5 |
| dry yeast cell powder | 1 |
| $CaCO_3$ | 0.4 |
| $MgSO_4 \cdot 7H_2O$ | 0.2 |
| KCl | 0.2 |
| $K_2HPO_4$ | 0.05 |
| Antifoam (silicon) | 0.05 |
| pH | 7.5 |

Fermentation flasks were incubated on a rotary shaker (set at 220 rpm) at 28° C. for 4 to 10 days. The whole broth was harvested. Extraction was carried out with three times MeOH addition, the broth was then sonicated for 20 min. The sample was filtered with Whatman filter no-1. Filtrate was collected and analyze for activity by HPLC.

HPLC: Analysis was performed using Shimadzu LC2010HT system with UV detector at 266 nm on a 250×4.6 mm, C-18 column with a mobile phase consisting of 50% acetonitrile in water containing 0.1% phosphoric acid at a flow rate of 1.0 ml/min. An HPLC chromatogram of a crude product (retention time ~28 min) is shown in FIG. 1. In this example the crude yield of fidaxomicin was about 1400 mg/L after 8 days.

Example-2

After sterilization conditions (40 min., 121° C., 1.05 kg/cm$^2$) the seed flask (250 ml) containing medium M-1 NS2 (30 ml) was inoculated with *Actinoplanes deccanensis* and incubated on shaker (set at 220 rpm) at 28° C. for 24-28 hrs. One percent vegetative growth from the first passage seed flask was then transferred aseptically to a seed flask containing the same ingredients as in medium M-1 NS2 (200 ml in 1000 ml flask) and was incubated on rotary shaker (set at 220 rpm) at 28° C. for 24-28 hrs. Five percent vegetative growth from the second passage seed flasks was then used to inoculate with *Actinoplanes deccanensis* in a 50 lit fermenter containing medium. M-1 NP1 (30lit).

Batch size: 30 lit
Sterilization: 121° C., 1.05 kg/cm$^2$, 40 minutes
Incubation temperature: 28° C.
Aeration rate: 0.5-1.5 volumes of air per volume of medium per minute
Tip speed: 1.0-3.7
Dissolve oxygen level should be maintained at around 40%.
PMV (packed mycelia volume) was monitored at 3000 rpm for 10 minutes in bench top centrifuge in conical bottom tube. The fermentation was carried out for 4-10 days and the broth was harvested.

Example-3

Figure 2:
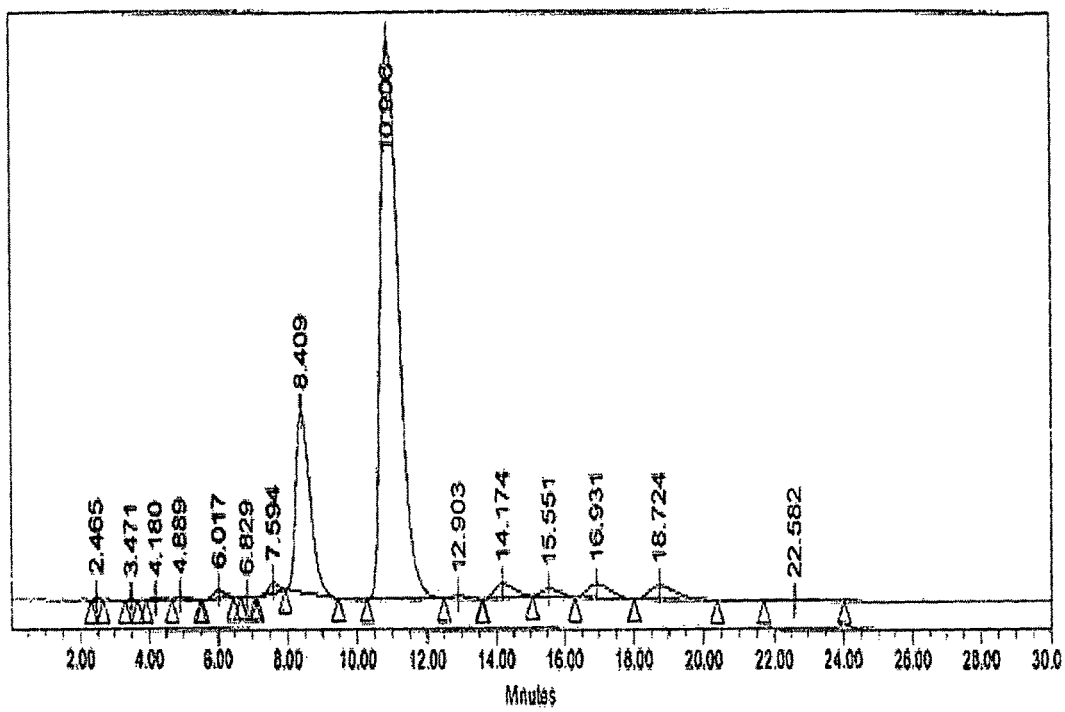
FIG. 2 refers to HPLC chromatogram showing yield of fidaxomicin obtained in Example 3.

Fermentation broth containing fidaxomicin as obtained in Example-2 (30 liter) was taken in a reactor. pH was adjusted to about 7. Ethyl acetate (30 liter) was added to the broth at a room temperature. The mixture was stirred at a room temperature and then ethyl acetate layer containing fidaxomicin was separated. The extraction was repeated with (30 liter) of ethyl acetate. Ethyl acetate layers were combined and washed with water (10 liter). Ethyl acetate was evaporated under vacuum to give oily residue. Ethyl acetate was added to the obtained residue and the solution was stirred for 30 min at 40° C. Petroleum ether was added to the solution and stirred for 2 hr. The precipitate was filtered and washed with petroleum ether. In this example the crude yield of fidaxomicin was about 1500 mg/L. (FIG. 2)

Crude fidaxomicin was purified by prep-HPLC method as described below:
Apparatus: Knauer Preparative HPLC K1950
Column: C18, 250×50 mm, 16 microns
Detector: UV detector at 254 nm
Injection volume: 50 ml (2 gm)
Flow rate: 60 ml/min
Run time: 200 minutes
Diluents: Methanol
Mobile phase: A:B (55:45) A—Water containing 2% acetic acid; B—Acetonitrile 25% NaCl solution was added to the obtained fractions and layers were separated. Solvent was evaporated to give residue. 1 gm of the product obtained was dissolved in ethyl acetate (10 ml) at a temperature of 40° C. to get a clear solution. 15 ml of petroleum ether was added to the solution. The solution was maintained at a room temperature for about 3 hr. The precipitate obtained was filtered, washed with petroleum ether and dried under vacuum to give pure fidaxomicin.

Figure 3:
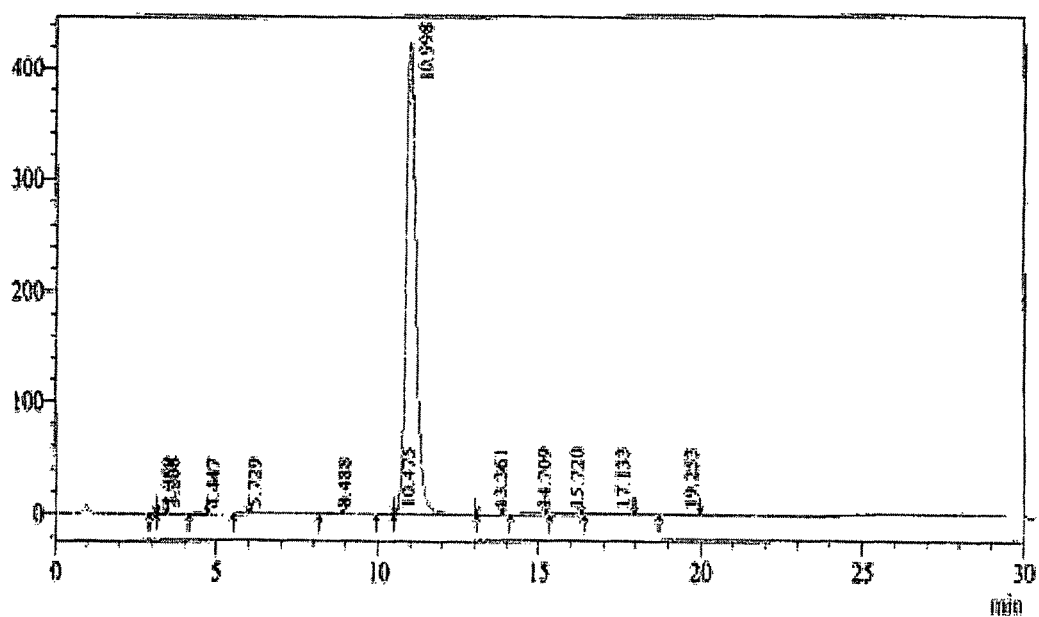
FIG. 3 refers to HPLC chromatogram showing purity of fidaxomicin obtained in Example 3.

Pure fidaxomicin, thus obtained has purity of 99.18% by area HPLC as shown in FIG. 3. (Method: Purity was determined on Shimadzu LC 2010 using C18, 5 micron, 150×4.6 mm column. Wavelength: 266 nm; Flow rate: 1.5 ml/min; Mobile phase: Acetonitrile: 0.1% ortho phosphoric acid (50:50)).

We claim:

1. A process for the production of fidaxomicin comprising:
   providing a culture medium consisting essentially of,
   about 0.1% to about 15% wt of sorbitol,
   about 0.1% to about 10% wt of corn gluten,
   about 0.1% to about 15% wt of cane sugar,
   about 0.1% to about 5% wt of glycerol,
   about 0.1% to about 5% wt of soybean oil,
   about 0.1% to about 5% wt of soybean powder,
   about 0.1% to about 5% wt of dry yeast cell powder,
   about 0.05% to about 3% wt of $CaCO_3$,
   about 0.05% to about 2% wt of $MgSO_4 \cdot 7H_2O$,
   about 0.05% to about 2% wt of KCl, and
   about 0.01% to about 1% wt of $K_2HPO_4$;
   culturing a fidaxomicin producing microorganism using the culture medium to produce a fidaxomicin containing whole broth, wherein the fidaxomicin containing whole broth is produced without the use of an adsorbent resin;
   extracting the fidaxomicin containing whole broth using a water immiscible organic solvent, wherein fidaxomicin is extracted into the water immiscible organic solvent from the fidaxomicin containing whole broth;
   separating the water immiscible organic solvent layer;
   isolating the fidaxomicin from the water immiscible organic solvent layer, wherein the crude fidaxomicin is produced in a yield of greater than 1000 mg/L of broth; and
   purifying the isolated fidaxomicin using any one or more of column chromatography, preparative HPLC, and crystallization to produce fidaxomicin having a purity of greater than 98% when measured by HPLC.

2. A process according to claim 1, wherein the step of culturing is performed at a temperature from about 20° to about 35° C. and at a pH of about 5 to about 8.

3. A process according to claim 1, wherein the water immiscible organic solvent is selected from an ester, an aromatic or aliphatic hydrocarbon, a $C_4$-$C_8$ alcohol, or a mixture thereof.

4. A process according to claim 1, wherein the water immiscible organic solvent is selected from one of ethyl acetate, isopropyl acetate, butyl acetate, toluene, isobutanol, or a mixture thereof.

5. A process according to claim 1, wherein the fidaxomicin producing microorganism is *Actinoplanes deccanensis*.

* * * * *